(12) United States Patent
Kim (10) Patent No.: US 11,766,513 B2
(45) Date of Patent: Sep. 26, 2023

(54) SYSTEM AND METHOD FOR REMOVAL OF GASTRIC AIR FROM PREMATURE INFANTS ON NASAL CPAP

(71) Applicant: The Regents of the University of California, Oakland, CA (US)

(72) Inventor: Jae H. Kim, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1068 days.

(21) Appl. No.: 16/340,425

(22) PCT Filed: Oct. 10, 2017

(86) PCT No.: PCT/US2017/055934
§ 371 (c)(1),
(2) Date: Apr. 9, 2019

(87) PCT Pub. No.: WO2018/068052
PCT Pub. Date: Apr. 12, 2018

(65) Prior Publication Data
US 2019/0262513 A1 Aug. 29, 2019

Related U.S. Application Data

(60) Provisional application No. 62/405,959, filed on Oct. 9, 2016.

(51) Int. Cl.
*A61M 1/00* (2006.01)
*A61J 15/00* (2006.01)
*A61M 16/00* (2006.01)

(52) U.S. Cl.
CPC .............. *A61M 1/84* (2021.05); *A61J 15/00* (2013.01); *A61M 1/73* (2021.05); *A61M 1/743* (2021.05);

(Continued)

(58) Field of Classification Search
CPC .................. A61M 2240/00; A61M 2205/3344
See application file for complete search history.

(56) References Cited

U.S. PATENT DOCUMENTS

| | | | | |
|---|---|---|---|---|
| 4,813,931 A | * | 3/1989 | Hauze | ................... A61M 1/784 604/319 |
| 2010/0030133 A1 | * | 2/2010 | Elia | ...................... A61B 5/4836 604/35 |

(Continued)

OTHER PUBLICATIONS

Walor D, Berdon W, Anderson N, Holt PD, Fox M., "Gaseous distention of the hypopharynx and cervical esophagus with nasal CPAP: a mimicker of pharyngeal perforation and esophageal atresia." Pediatr Radiol. Dec. 2005;35 (12):1196-8. Epub Aug. 12, 2005. PMID: 16096824 [PubMed—indexed for MEDLINE].

(Continued)

*Primary Examiner* — Jenna Zhang
(74) *Attorney, Agent, or Firm* — Kaplan Breyer Schwarz, LLP; Stuart H. Mayer (57) ABSTRACT

Systems and methods according to present principles meet the needs of the above in several ways, and in particular provide a product that can continuously monitor and remove air from the stomach without removing liquid from a premature neonate's stomach. The device works by providing suction pressure of, e.g., 10±0.1 mmHg through the feeding tube to continuously remove air from the stomach. In this way the device prevents the problem of gastric distension all together. The pressure may be regulated by using an electronic control valve.

7 Claims, 9 Drawing Sheets

(52) U.S. Cl.
CPC ............... *A61M 1/80* (2021.05); *A61M 16/00* (2013.01); *A61M 2202/02* (2013.01); *A61M 2205/3344* (2013.01); *A61M 2210/1053* (2013.01); *A61M 2240/00* (2013.01)

(56) References Cited

U.S. PATENT DOCUMENTS

| | | | |
|---|---|---|---|
| 2012/0132216 A1* | 5/2012 | Vaska | A61F 5/566 128/848 |
| 2016/0067148 A1* | 3/2016 | Nordquist | A61J 15/0003 604/28 |

OTHER PUBLICATIONS

J.C. Jaile, "Benign Gaseous Distension of hte Bowel in Premature Infants Treated with Nasal Continuous Airway Pressure: A study of Contributing Factors" ARJ: 158, Jan. 1992.

* cited by examiner

1) STEADY STATE AIR REMOVAL

FIG. 8A

2) INTERMITTENT INJECTION

FIG. 8B

3) WALL SUCTION AND RELEASE

SYSTEM AND METHOD FOR REMOVAL OF GASTRIC AIR FROM PREMATURE INFANTS ON NASAL CPAP

CROSS-REFERENCE TO RELATED APPLICATIONS

This application is a national stage application, filed under 35 U.S.C. § 371, of International Patent Application No. PCT/US17/55934 filed on Oct. 10, 2017, entitled, "SYSTEM AND METHOD FOR REMOVAL OF GASTRIC AIR FROM PREMATURE INFANTS ON NASAL CPAP", which claims benefit of priority of U.S. Provisional Patent Application Ser. No. 62/405,959, filed Oct. 9, 2016, entitled "SYSTEM AND METHOD FOR REMOVAL OF GASTRIC AIR FROM PREMATURE INFANTS WHO ARE ON NASAL CONTINUOUS POSITIVE AIRWAY PRESSURE SUPPORT", owned by the assignee of the present application and herein incorporated by reference in its entirety.

BACKGROUND

Premature infants are continuously fighting to live, and any small harm can mean death. They often cannot breathe on their own and continuous positive airway pressure (CPAP) constitutes one way to provide the breathing support they need, and is a better method than the previously used endotracheal intubation method. A CPAP machine delivers compressed air to the nose mask and keeps the airway open under air pressure, which allows for unobstructed breathing to take place.

However, there are instances when the air breathed in by preterm infants finds its way into the baby's stomach, instead of the lungs, causing gastric distension. The extra air in the infants' stomach can inflate the stomach with air, cause babies discomfort and inability to eat, and can even rupture or perforate the stomach or bowels.

One solution to this gastric complication is to use a syringe extraction through a feeding tube. The nurse attaches a syringe to a feeding tube and suctions out the air. The problem with this method is twofold. First, the air in the stomach is not detected until a nurse sees the inflated midsection of the baby. This is problematic as there may already be potential complications and discomfort. The other problem is that once the distension of the stomach is noticed, siphoning the air out is very difficult to do without also sucking up stomach liquids.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways, and in particular provide a product that can continuously monitor and remove air from the stomach without removing liquid from a premature neonate's stomach.

The device works by providing suction pressure of, e.g., 10±0.1 mmHg through the feeding tube to continuously remove air from the stomach. In this way the device prevents the problem of gastric distension all together. The pressure may be regulated by using an electronic control valve.

In one aspect, the invention is directed towards a device for removal of gases, configured for insertion in the stomach of an infant, the device including: a catheter, the catheter having an interior and including a distal end configured for insertion into the stomach of an infant, the distal end including one or more holes for perforations configured to allow air from the stomach to enter the holes and the interior of the catheter, the catheter further including a proximal end; a pressure sensor disposed on the catheter, the pressure sensor in pressure communication with a pressure in the stomach; a source of negative pressure, the source of negative pressure in pressure communication with the interior of the catheter; and a pressure regulator in signal communication with the pressure sensor and the source of negative pressure, such that the pressure regulator controls the negative pressure in the interior of the catheter.

Implementations of the invention may include one or more of the following. The pressure regulator may be configured to detect if the negative pressure in the interior of the catheter has a magnitude greater than a threshold level, and if so, may be configured to at least temporarily shut off the source of negative pressure. A plurality of perforations or holes may be defined in the distal end of the catheter. The pressure regulator may be configured to keep the negative pressure in the interior of the catheter at a desired threshold, plus or minus a desired tolerance. The catheter may be coupled to a feeding tube. The catheter may form a portion of a feeding tube, or a CPAP machine. The device may further include a catch for receiving liquids or solids that are suctioned out of the stomach.

In another aspect, the invention is directed towards a method for removal of gases in the stomach of an infant, including: inserting a catheter into the stomach of an infant, the catheter having an interior and including a distal end including one or more holes for perforations configured to allow air from the stomach to enter the holes and the interior of the catheter, the catheter further including a proximal end, the catheter further including a pressure sensor disposed thereon, the pressure sensor in pressure communication with a pressure in the stomach; operating a source of negative pressure, the source of negative pressure in pressure communication with the interior of the catheter; and regulating the source of negative pressure, a level of pressure controlled by a pressure regulator in signal communication with the pressure sensor and the source of negative pressure, such that the pressure regulator controls the level of negative pressure in the interior of the catheter to within a predetermined range of negative pressures.

Implementations of the invention may include one or more of the following. The predetermined range may be, compared to ambient pressure, −10 mmHg+/− a predetermined tolerance. The predetermined tolerance may be 10% or 5%. The method may further include monitoring the negative pressure in the interior of the catheter. The method may further include detecting if the negative pressure in the interior of the catheter has a magnitude greater than a threshold level, and if so, causing the pressure regulator to at least temporarily shut off the source of negative pressure. The catheter and holes may be configured to remove air from an infant's stomach but not liquids. The pressure regulator may be an electronic control valve.

Advantages of the invention may include one or more of the following. Systems and methods according to present principles can be used in hospitals across the world to help save the lives of premature infants. Systems and methods according to present principles can also be modified and used for children or adults who suffer from respiratory conditions who also use the CPAP machine. The device and its derivatives may be capable of clearing excess gas trapping in premature infants who are on CPAP during their first few weeks of life, which would involve most infants less than 2000 grams birth weight in all neonatal units. This is approximately 5% of all births in the US. The current trend is for more infants to be placed on CPAP and there is an increasing number of preterm births each year. The unique catheter designs may be used once for each patient but can stay in for up to 30 days as per standard guidelines. The suction device may be reusable but required for each bedside. The device may suction out air through a feeding tube while the feeding tube is or is not in use.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

DETAILED DESCRIPTION

Systems and methods according to present principles provide continuous negative (vacuum) suction from the stomach of premature infants who are on continuous positive airway pressure (CPAP) support. It eliminates accidental air trapping that occurs in infants on CPAP that can lead to deleterious effects in or on the bowels of these infants. It can also sense and regulate the amount of negative pressure to ensure controlled pressure is applied at all times.

While there are various vacuum devices to provide suction for infants there are no devices that provide very low and tightly controlled negative pressure. Furthermore, there are no devices that sense and regulate negative pressure and do so with the sensitivity of systems and methods according to present principles.

Current apparatuses include passive standard suction catheter and traps as well as low Gomco suction devices for post surgical decompression of the stomach. These are available in most hospitals. Neither method is suitable for decompression at low levels and to enable feeding while on suction.

Systems and methods according to present principles achieve the goal of increasing access to free air, have more access points to the air, and finally offer active suction of the free air.

In more detail, in one implementation, a catheter incorporates one or more holes and is placed into the stomach in a similar way as an orogastric or nasogastric tube. Changes in shape or material can increase the exposure of the holes in the catheter to the free air, thereby increasing chances for gas extraction. In the case of active suction, the catheter is attached to a suction regulator that controls and administers a low amount of continuous negative pressure. The regulator may derive suction from a standard wall vacuum provided in the hospital. The regulator may also sense the pressure and regulate the flow so as to maintain a low amount of constant negative pressure, or an amount that is constant to within a predetermined tolerance. The low pressure may be just sufficient to remove gas trapping in the stomach without removing stomach liquid or affecting milk feeding.

Systems and methods according to present principles have been shown in some implementations to successfully complete the following three tests: suction air out of a human stomach test model while open to the atmosphere, suction air out while closed to the atmosphere and while air is being injected to the human stomach test model, and detect when there is wall suction or when the feeding tube has become attached to the wall of the human stomach test model.

Figure 1:
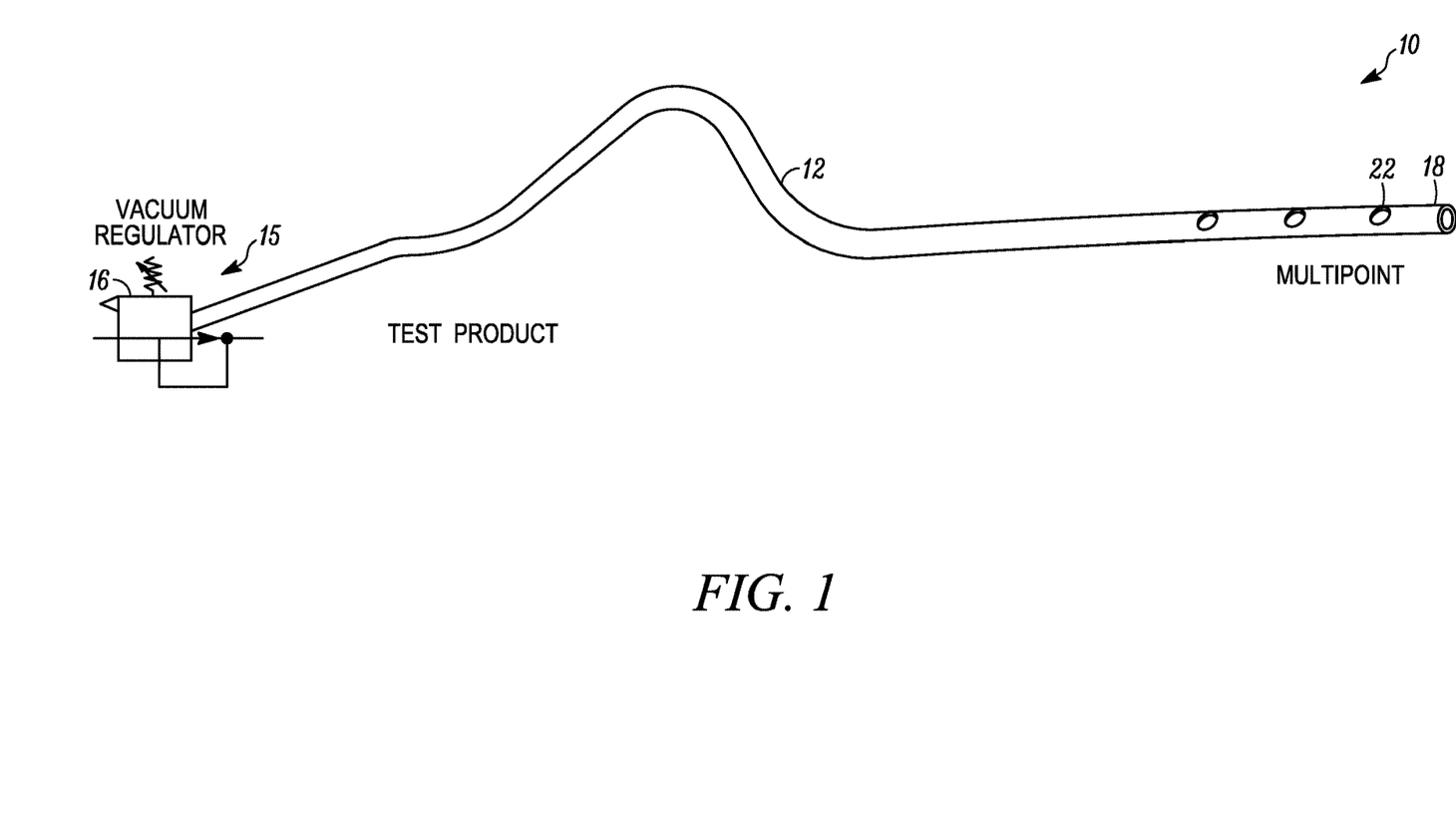
FIG. 1 is a schematic depiction of an implementation of a device according to present principles.

One implementation of an exemplary device 10 is as shown in FIG. 1. This implementation includes a regulator 16 and tubing 12 that provides multiple ports 22 spaced out throughout the stomach. The device 10 may extend between the proximal end 15 and a distal end 18

Figure 2:
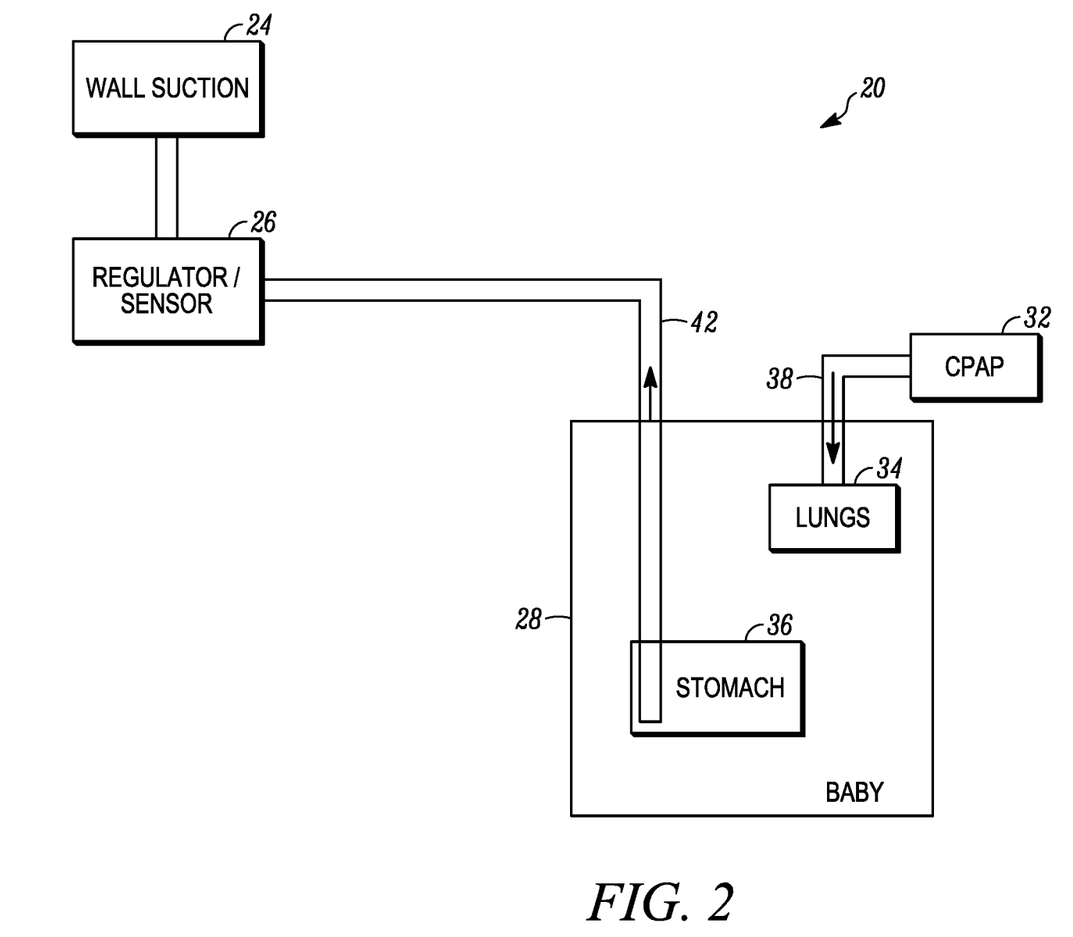
FIG. 2 is a schematic depiction of an implementation of a device according to present principles.

The device may be employed in a configuration as shown in FIG. 2, which shows a system 20 including a regulator/sensor 26 coupled to a source of wall suction 24. The human system 28 with lungs 34 is shown coupled to CPAP machine 32 through line 38. The stomach 36 of the patient is accessed through line 42, and the regulator/sensor 26 and source of negative pressure 24 allow the removal of air from the stomach 36.

In more detail, the device works by providing suction pressure of a desired value, e.g., 10±0.1 mmHg, through the feeding tube to continuously remove air from the stomach, thus the device prevents the problem of gastric distension all together.

Figure 3:
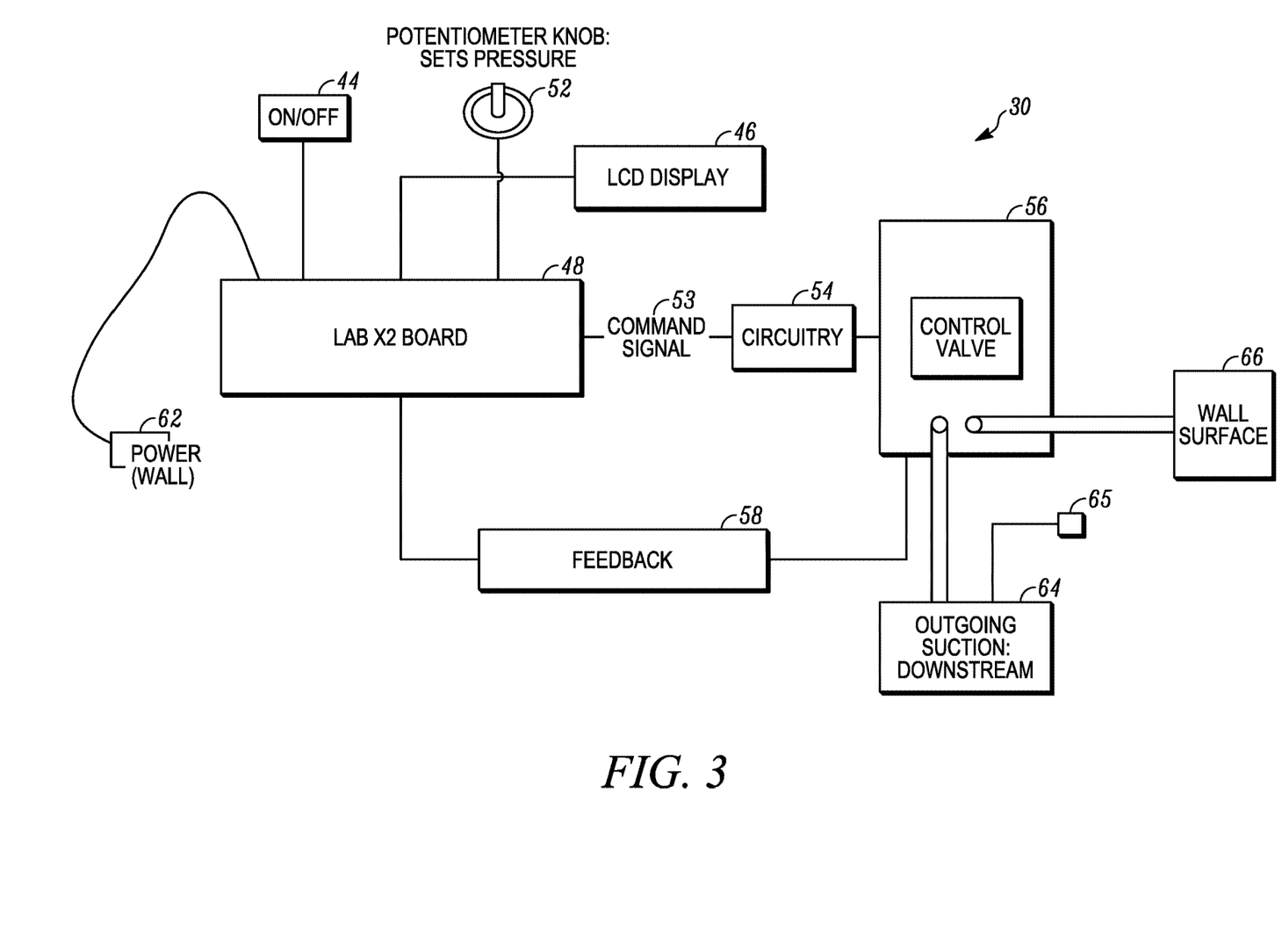
FIG. 3 is a schematic depiction of an implementation of a device according to present principles.

The pressure may be regulated by a control system that includes an electronic control valve 56, and a microcontroller on a LAB X2 board 48 (see the feedback control system shown in FIG. 3 below).

In this figure, the board 48 includes an on-off switch 44 and a source of power 62. A potentiometer knob 52 allows the setting of the pressure. An LCD display 46 may be employed to indicate various aspects of the system, including the negative pressure set. The board 48 transmits control signals or commands 53 to circuitry 54, which in turn operates the control valve 56. The control valve 56 is coupled to a source of negative pressure such as wall suction 66. The control valve is also couple to outgoing suction downstream 64, which is in turn coupled to a pressure transducer 65. The signal from pressure transducer 65 may be routed as feedback 58 to the board 48, and such feedback may be routed through the control valve 56.

The microcontroller on board 48 obtains information from an internal valve pressure transducer, which measures the pressure of the air in the downstream tube (feeding tube). Using th this e information the microcontroller on board 48 obtains from the pressure transducer, the microcontroller sends a signal 53 to command the valve 56 in its operation. Depending on the pressure of the air in the downstream tube 64, the microcontroller sends a signal to the valve 56 to shut-off or continue at the pressure it is.

Figure 4:
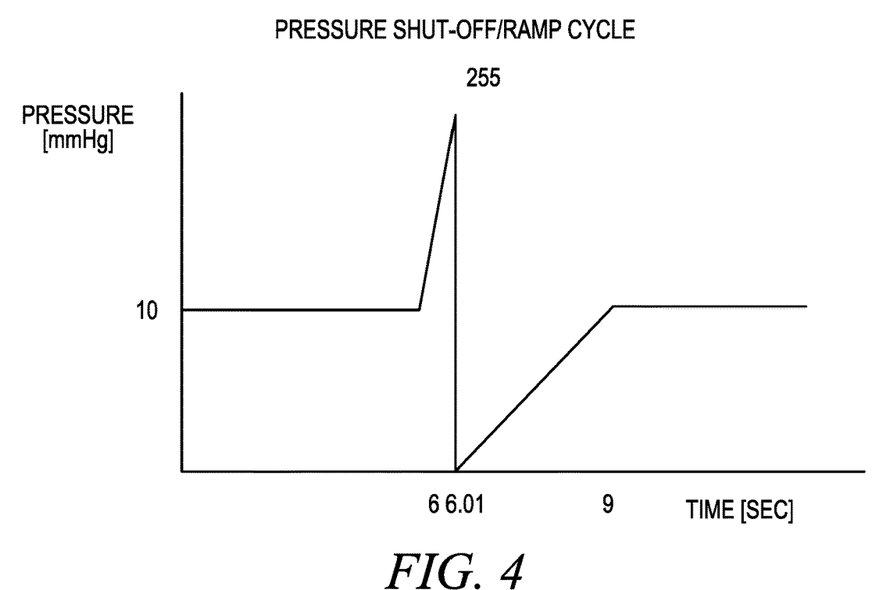
FIG. 4 is a depiction of logic which may be employed in a device according to present principles.

In one implementation, the code for the LAB X2 board 48 may follow the logic shown in FIG. 4 below. The pressure transducer will generally record a high pressure when there is wall suction or when the feeding tube is suctioning the esophagus or stomach lining. The code, thus, has a critical pressure input that makes the microcontroller shut-off the control valve to prevent damage to the preterm neonates.

This critical pressure may be in the range of, e.g., −50 to −80 mm Hg.

Figure 5:
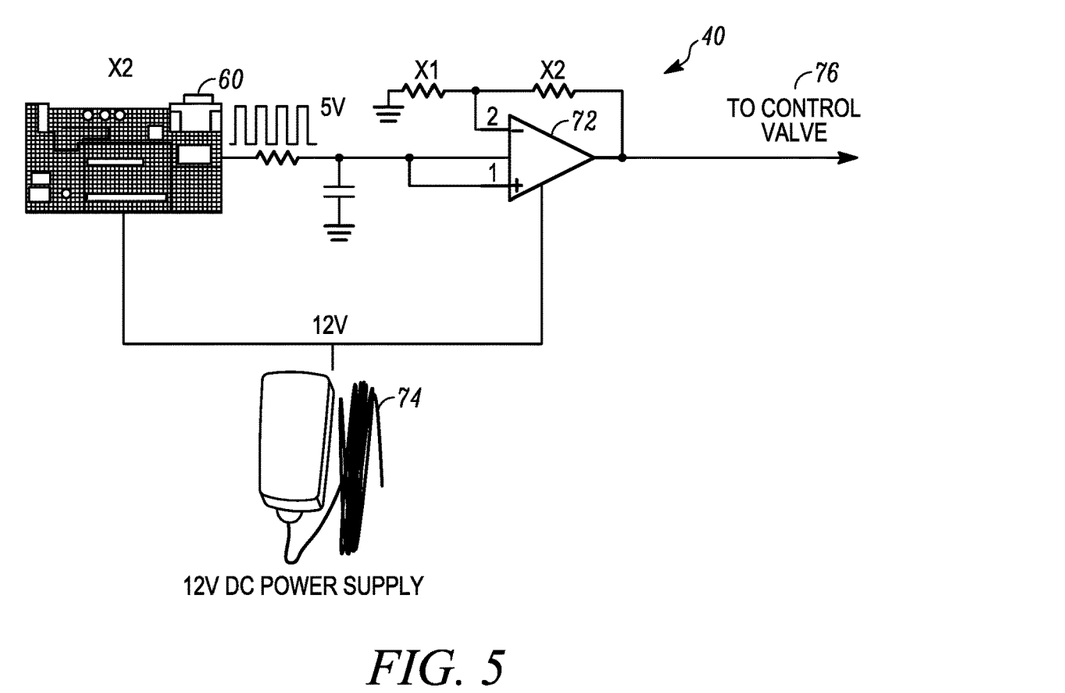
FIG. 5 is a schematic depiction of an implementation of a device according to present principles.

A circuit diagram to obtain a 0 to 10 volt command signal from the LAB X2 board 48 is shown in FIG. 5 below, which shows an electronic circuit to output 0-10 V. In this figure, the board 68 is powered by a power supply 74 in the same drive an operational amplifier 72 which in turn drives the control valve 76.

The device shown in FIG. 5 provides an adjustable negative pressure of 10±0.1 mmHg, controls pressure autonomously, and suctions out air but not liquid (food). This is possible because the low suction permits air to be released and any excessive suction that exceeds the threshold set on the device will turn off the suction and prevent fluids from being suctioned at the same time. Also, the tubing used to suck out the air may be integrated with the feeding tube and contain a "catch" for the fluids that are suctioned.

Safety of infants is paramount, and thus the device is required to perform its job without causing harm to infants. Thus, the device should provide the adjustable negative pressure with only a, e.g., ±0.1 mmHg tolerance. If the pressure becomes too high, severe damage can be caused to the infant and the consequences can be fatal. Thus, the device may be programmed such that it shuts off when it reaches the critical pressure. The machine is then able to turn back on within seconds of shutting off. For the safety of the infant and their health, the machine is able to continuously suction air out of the preterm neonates' stomachs to avoid gastric complications, and is also able to avoid the critical pressure.

The continuous gastric decompression device may include software code to regulate the pressure, a valve, a programmed microcontroller, and the necessary electronics including the power supply within a box. On the outside, the box may contain an LCD screen, potentiometer knob to set the pressure, and an on-off switch.

The system may advantageously use a digital control valve with a feedback loop that can monitor and regulate the incoming pressure and have an accurate and consistent output pressure.

Another option is to use a digitally controlled vacuum pump. Such a pump may have several advantages. First of all, the only requirement for the device to run would be an electrical outlet. Secondly, there is less chance of perturbations existing at the outlet pressure.

In one implementation, an electronic control valve from ProportionAir was used. This valve has two solenoid controlled orifices that regulate the inlet and exit of an internal chamber. The chamber houses a pressure transducer and the microprocessor completes the feedback loop for the valve.

Figure 6:
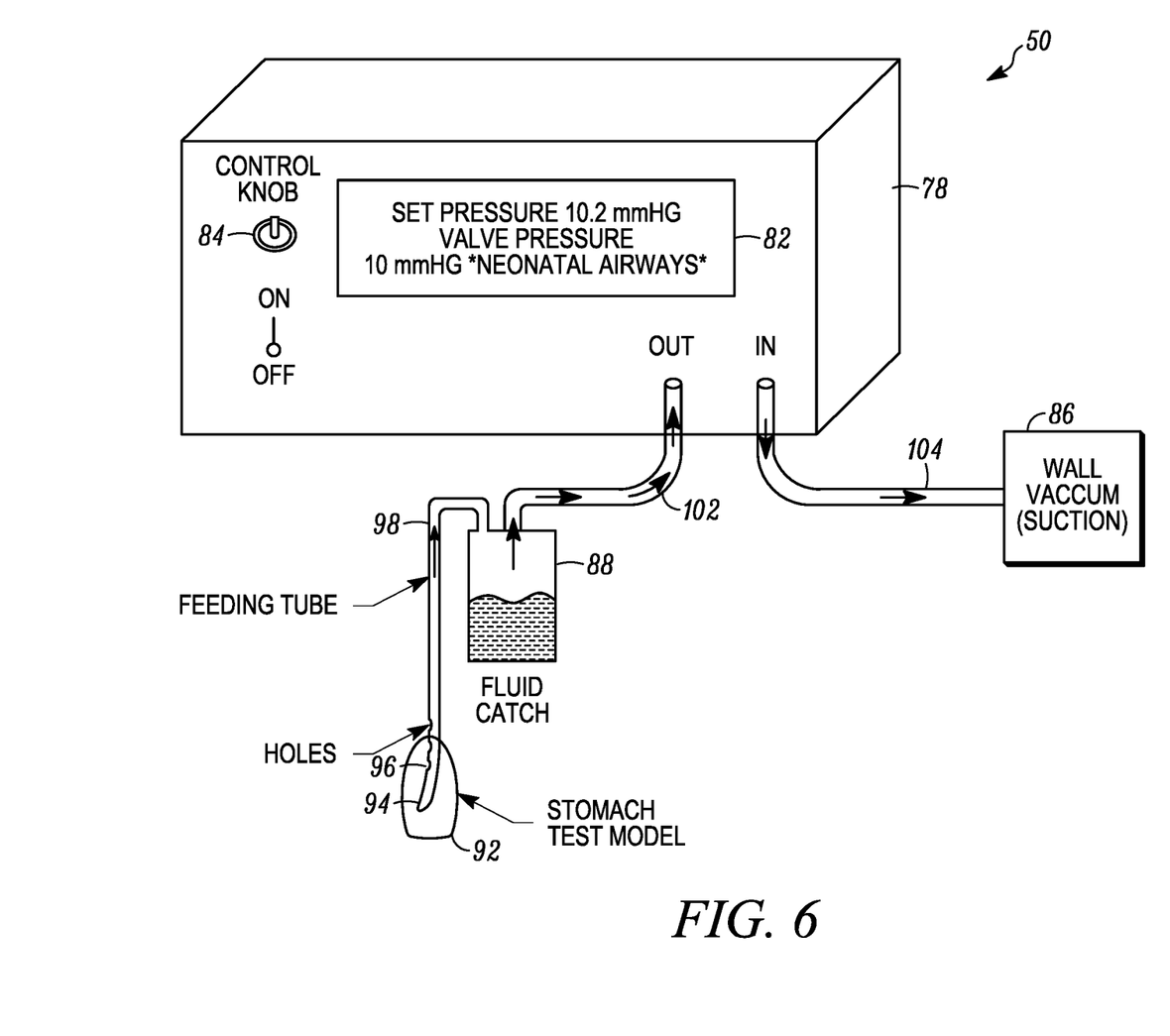
FIG. 6 is a schematic depiction of an implementation of a device according to present principles.

One implementation is shown in FIG. 6, which shows 1) tubing 104 (wall to valve) couple to the wall vacuum 86, 2) Control Valve 78 with accompanying, 3) Electronics and a display screen 82, 4) Fluid Catch 88, 5) Downstream tube 98, including a plurality of holes 94, 96, at a distal end, and finally a 6) Stomach Test Model 92.

Figure 7:
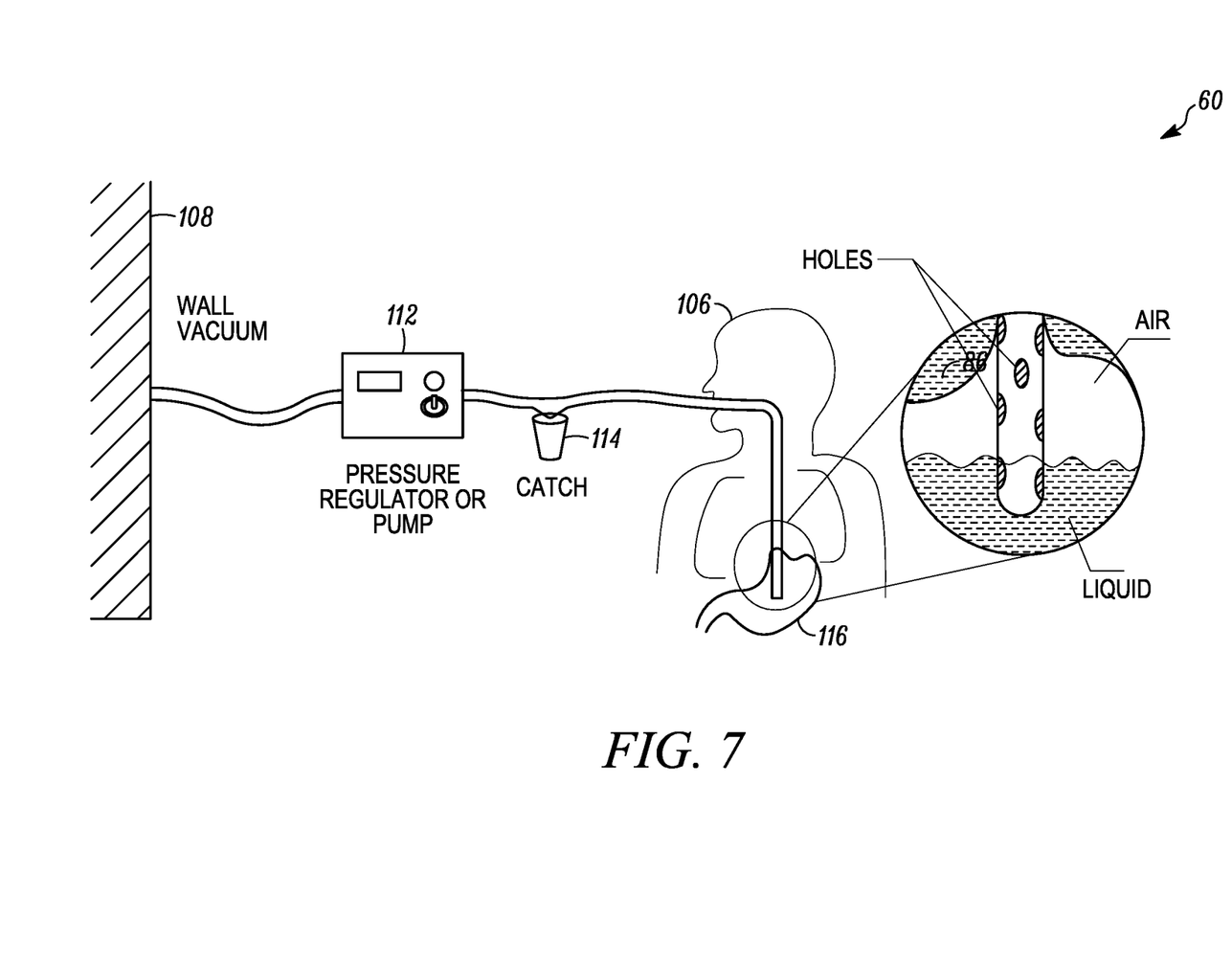
FIG. 7 is a schematic depiction of an implementation of a device according to present principles.

Referring to FIG. 7, the product 106 may include one or more of the following components: the control valve 112 coupled to the source of negative pressure 108, microcontroller with integrated circuitry within the control valve 112, tubing, controls, housing of components, LCD screen, fluid catch 114, and stomach test model 116. These components work in conjunction to extract air out of a neonate's stomach while meeting specific safety and functional parameters. Details of these components are described below in the context of a built prototype.

Control Valve

The control valve in one implementation is a ProportionAir MPV1 closed loop high resolution digital control valve. It is made up of two solenoid valves (inlet and exhaust), feeding chamber housing and an internal pressure transducer. There is also a preprogrammed controller to close the feedback loop and provide a robust system. The valve is factory calibrated to the desired specifications. Its input range is 0-160 mmHg. The output range is calibrated to 0-20 mmHg which will allow some tolerance around the targeted −10 mmHg suction pressure which is ideal for a premature baby. The valve is commanded through a 0-10V signal which correlates to the outlet range, i.e., a 5V signal will generate an outlet pressure of −10 mmHg. The valve may also employ a panel mount kit for mounting within the housing, and controls for an adjustable hysteresis band and system stability.

Pressure Transducer

In order to sense the downstream pressure, a pressure transducer was integrated into the product, e.g., a DS series vacuum transducer from ProportionAir, which measures pressure through a strain gauge located inside. The electrical output is a linear ratio of the pressure sensed in the 0-10V format, which is the same as the control valve command signal. Also like the control valve, the pressure range is calibrated to the desired outlet pressure.

Program

The program for running the device is divided into several parts. The first part defines the parameters for the X2 board, sets up the ports for input or output, includes files that are necessary for certain commands, and initializes the LCD. The program then goes into the main loop. The first part of the main loop takes the inputs such as the control knob and monitor signal and outputs those values to the LCD. The program also outputs the set pressure to the control valve to suck the air with the negative pressure. The program then reviews the blockage criteria if the internal valve pressure is greater than a max pressure defined earlier in the program. If it goes into this portion, the program tells the control valve to shut down for a defined amount of time. Upon startup it goes through a for loop which ramps the pressure back up to the set value. Whether or not the program detects a blockage, at this point it returns to the beginning of the main loop and starts the process over.

The flow of air in the feeding tube and in the stomach of a premature neonate is assumed to be very small. It is also assumed that the air behaves like an ideal gas. Another assumption is that the suctioning will occur in conditions that are closed to the atmosphere with a continuous influx of air at relatively low speed. The ideal gas law is described by the equation:

$$pV=nRT$$

where p is the absolute pressure of the gas, V is the volume of the gas, n is the number of moles of gas, R is the universal gas constant, and T is the absolute temperature.

From fluid mechanics it is known that a change in elevation z2–z1 is equivalent to a change in pressure (p2–p1)/γ, where z is the height, p is the pressure, and γ is the specific weight of the fluid. For these purposes, the γ of water and air were taken to be 9790 N/m3 and 11.8 N/m3 respectively. Since air in the device is moving at extremely low speeds, air is assumed to be incompressible.

The device was tested under three conditions: with the human test model open to the atmosphere, closed to the atmosphere with no incoming air, and closed to the atmosphere while air was being injected. All three tests contained water inside the test model chamber. The tests were performed with the feeding tube's holes (ports) alternatively fully submerged in water, partially submerged in water, and fully open to the atmosphere.

Figure 8A:
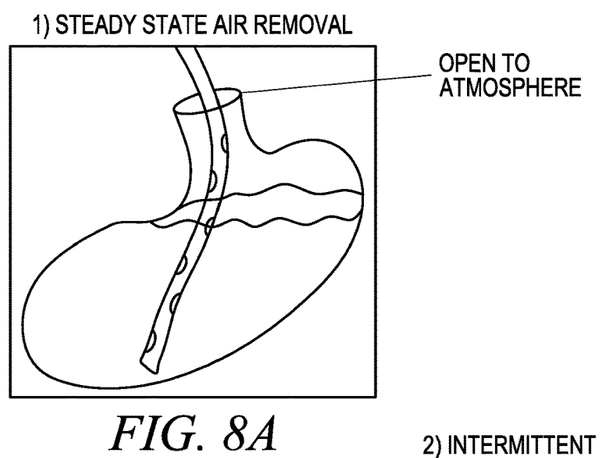
FIG. 8A-8C show various tests conducted to demonstrate utility of implementations of a device according to present principles.
Figure 8B:
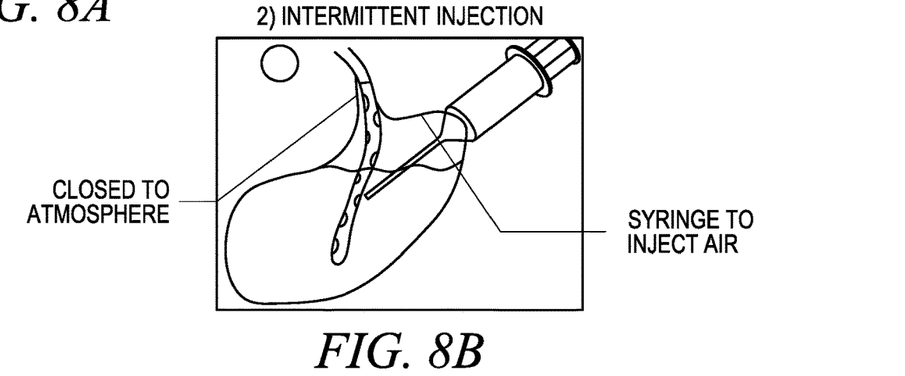
Figure 8C:
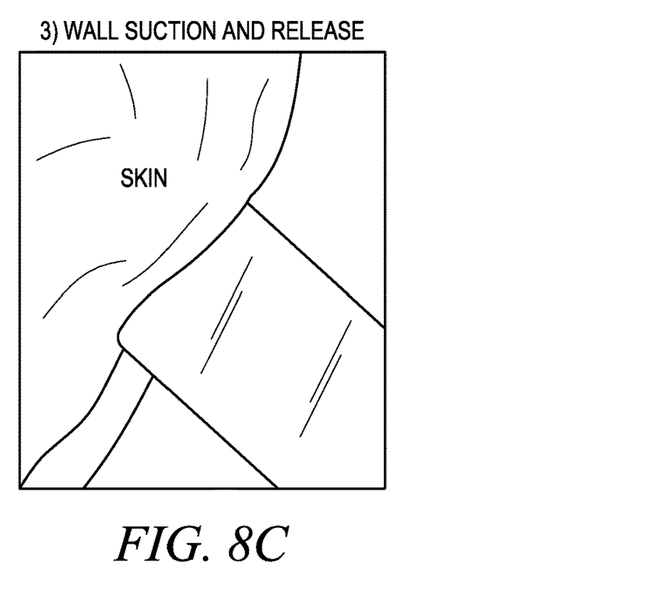

These tests are schematically shown in FIGS. 8A, 8B, and 8C.

Test 1 Steady State Air Removal

The purpose of test 1 (8A) was simply to show that the valve worked properly or that it was able to successfully suction air out of the human test model while the human test model was open to the atmosphere. For this test, an open cup filled with water and a balloon were used for the human test model; both test models produced similar results. The feeding tube was placed within the balloon (or cup) and the device was turned on. The air was suctioned out successfully, thus the balloon collapsed. The balloon remained collapsed when the ports of the feeding tube were opened to the atmosphere and when they were partially submerged in water. However, when the ports of the feeding tube were fully submerged in water, water was suctioned, causing the internal valve pressure to increase past the set threshold, which in turn caused the valve to shut off. This was due to the fact that when all the ports were fully submerged in water, the pressure needed to suction out or lift a column of water is much higher than that required to suction out air since the specific weight of water is much higher than that of air. At 10 mmHg of pressure, it was easy to suction out water if the ports were submerged in water. 10 mmHg of pressure is the desired set pressure. Thus, if all the ports in the feeding tube are submerged in water there is a problem. Optimizations may include optimizing the tube and the set pressure parameters to avoid the suctioning of liquid while at the same time being able to suction out air.

Test 2 Intermittent Injection

Test 2 was done while the human test model was closed to the atmosphere. The results of this test were particularly interesting. The balloon was initially filled with air. If all the ports of the feeding tube were open to the atmosphere, then the balloon disinflated quickly. However, even when only some of the ports were submerged in water, suctioning of water occurred. The suctioning of water caused the valve to shut off and then turn back on to try to clear the tube of water. This process of shutting off and clearing delayed the suctioning of air out of the human stomach test model. The difference between test 1 and test 2 is that in test 2 suctioning of water occurred even when just some of the ports were submerged in water. In test 1, the test model was open to the atmosphere and in test 2 it was not. These results are of particular interest because the actual usage conditions of the device will be closed to the atmosphere. Optimizations include the study and incorporation of results of air flow and pressure in very narrow tubes at low speeds.

Test 3 Wall Suction and Release

Test 3 was done with all the ports fully submerged in water. Test 3 was done to determine the minimum pressure required to suction water, and the minimum pressure required to clear a tube full of water when the ports were all in and out of the water. The results are summarized in the Table below. Test 2 also showed that the higher the column of water present in the feeding tube the longer it took to suction out the water or to clear the water. This makes sense because the more water there is the higher the weight will be, which implies the need of a higher pressure to remove or clear the water.

TABLE

Test Results: Pressure Requirements

| Objective | Set Pressure (mmHg +/− 1) |
| --- | --- |
| Pressure needed to get full column of water; ports fully submerged in water | 8.9 |
| Minimum pressure to clear column of water; ports opened to atmosphere | 15.0 |
| Clears full column of water quickly; ports are opened to atmosphere | 19.1 |

Figure 9:
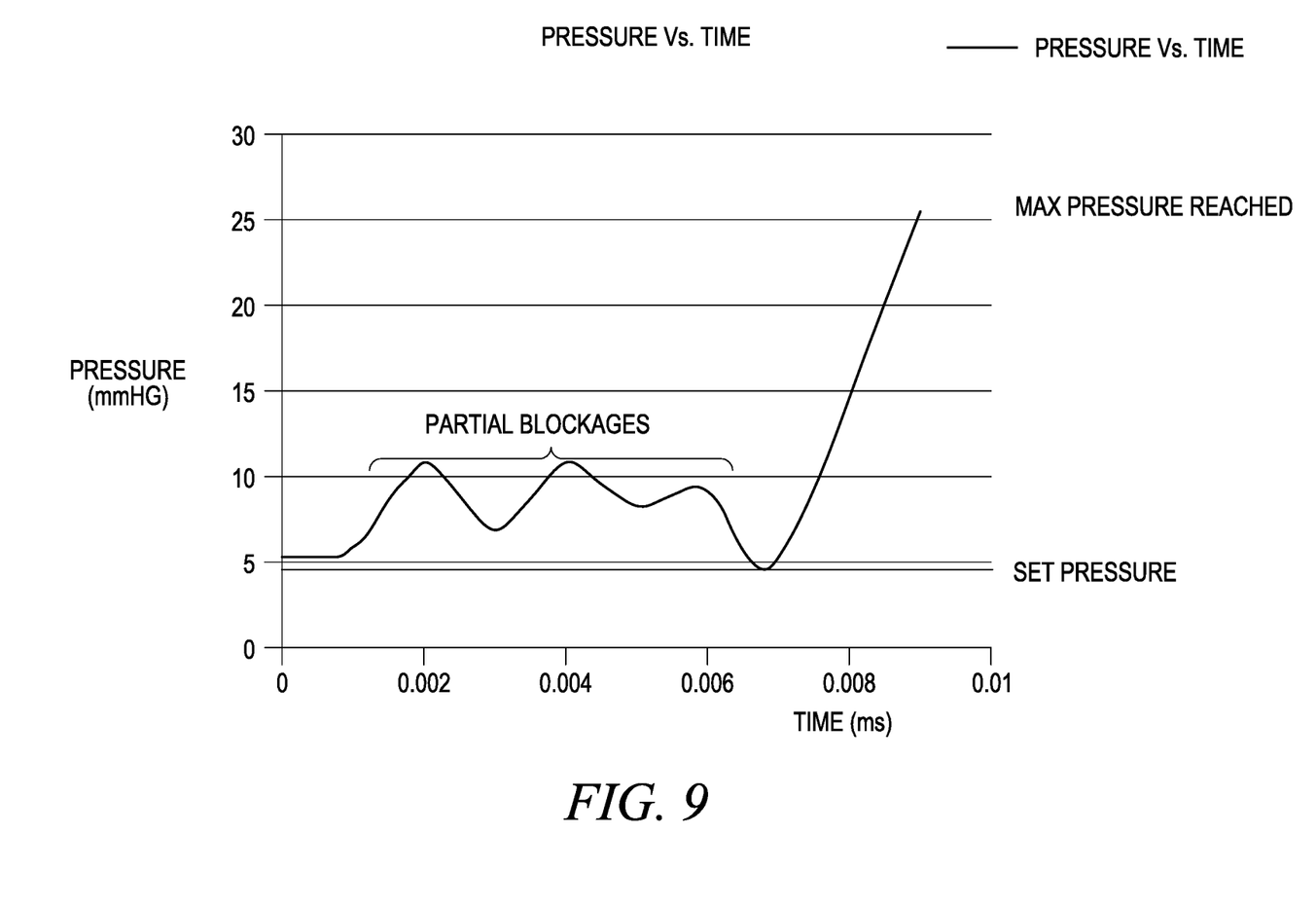
FIG. 9 illustrates how quickly a maximum pressure is reached when the ports of the feeding tube encounter wall suction or are submerged in water.
Figure 10:
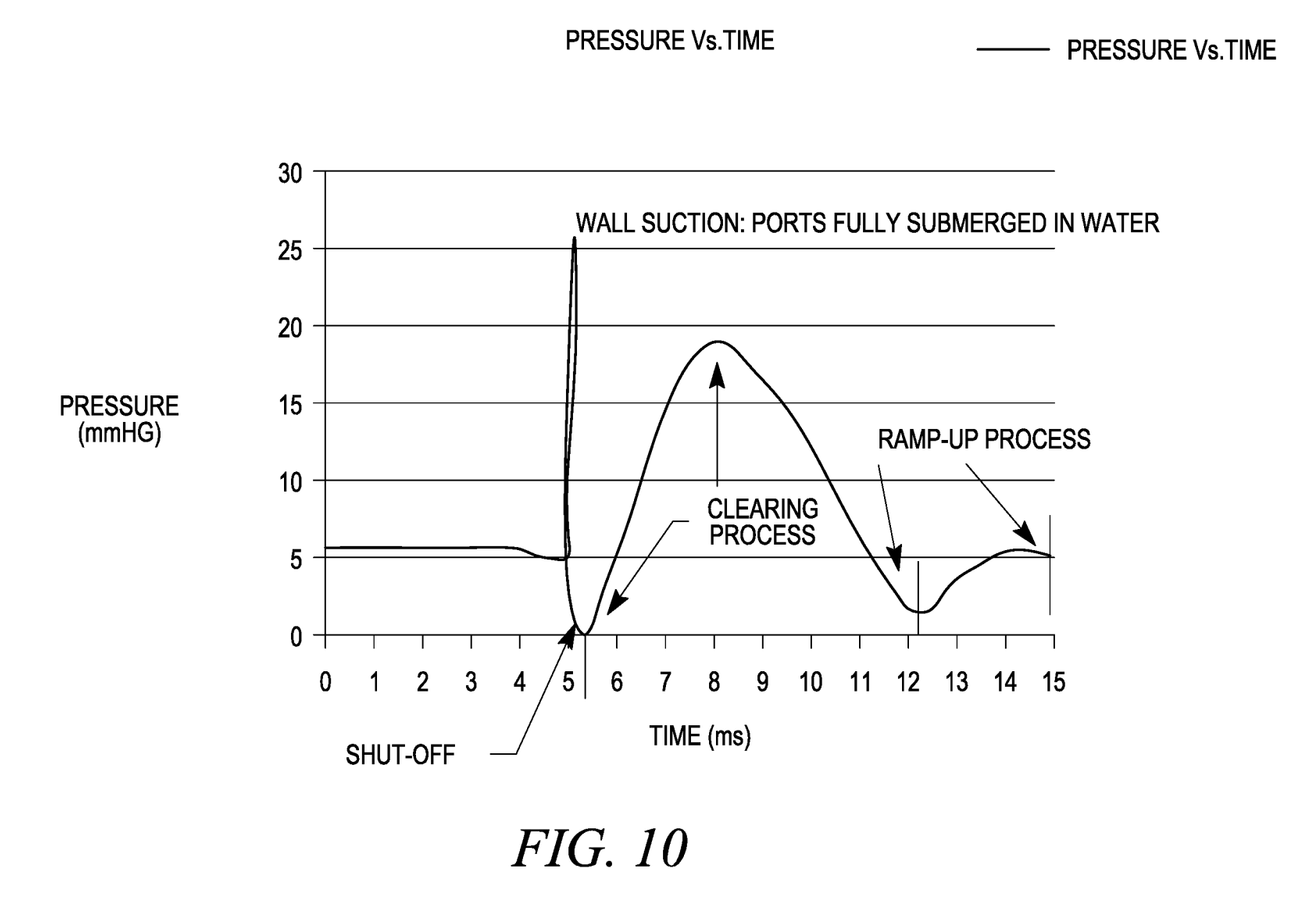
FIG. 10 shows the process the device goes through when there is wall suction or when the ports of the feeding tube are fully submerged in water.

FIG. 9 illustrates how quickly the max pressure is reached when the ports of the feeding tube encounter wall suction or when they are fully submerged in water. FIG. 10 shows the process the device goes through when there is wall suction or when the ports of the feeding tube are fully submerged in water. First, the valve shuts off, the pressure equates to zero, then it attempts to clear the tube by increasing the pressure to 19 mmHg, then once the tube is cleared the pressure decreases then it gradually increases or ramps up to the desired set pressure, which in the case of the figure below was 5 mmHg.

To operate the device, the power supply is connected to an electrical wall outlet. The tubing is connected from the wall pressure suction to the in connector. The downstream tubing is connected to the out connector. The switch is placed in the on position. The pressure is set to the desired pressure using the control knob which will display in the LCD screen.

In variations of the described systems and methods, devices may include alteration of the orogastric or nasogastric tube design to include additional perforated holes to allow for more access to the air in the stomach. Floatable materials may be used.

Additional optimizations of the design may include optimizing how the feeding tube should have the holes positioned to optimize the effects of the suctioning device, and should also optimize and update the program used to operate the device. Also, because of the suction of water when the valve shuts off, which is when the blockage criteria is met, an additional valve may be added that opens to atmospheric pressure when the shutoff is met. This will act in a similar manner as a "pull down resistor" in circuit theory and prevent problems due to water stuck in the tubing.

The system and method may be fully implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi-connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method.

While the invention herein disclosed is capable of obtaining the objects hereinbefore stated, it is to be understood that this disclosure is merely illustrative of the presently preferred embodiments of the invention and that no limitations are intended other than as described in the appended claims.

The invention claimed is:

1. A method for removal of gases in the stomach of an infant, comprising:
   a. inserting a catheter into the stomach of an infant, the catheter having an interior and including a distal end including one or more holes for perforations configured to allow air from the stomach to enter the one or more holes and the interior of the catheter, the catheter further including a proximal end, the catheter further including a pressure sensor disposed thereon, the pressure sensor in pressure communication with a pressure in the stomach;
   b. operating a source of negative pressure, the source of negative pressure in pressure communication with the interior of the catheter; and
   c. regulating the source of negative pressure, a level of pressure controlled by a pressure regulator in signal communication with the pressure sensor and the source of negative pressure, such that the pressure regulator controls the level of negative pressure in the interior of the catheter to within a predetermined range of negative pressures and if the level of negative pressure in the interior of the catheter has a magnitude greater than a threshold level that is sufficient to remove gas trapping in the stomach without removing stomach liquid, causing the pressure regulator to at least temporarily shut off the source of negative pressure.

2. The method of claim 1, wherein the predetermined range is, compared to ambient pressure, −10 mmHg +/−a predetermined tolerance.

3. The method of claim 2, wherein the predetermined tolerance is 10%.

4. The method of claim 2, wherein the predetermined tolerance is 5%.

5. The method of claim 1, further comprising monitoring the level of negative pressure in the interior of the catheter.

6. The method of claim 1, wherein the catheter and the one or more holes are configured to remove air from an infant's stomach but not liquids.

7. The method of claim 1, wherein the pressure regulator is an electronic control valve.

* * * * *